(12) United States Patent
Banton et al.

(10) Patent No.: US 7,763,876 B2
(45) Date of Patent: Jul. 27, 2010

(54) GLOSS AND DIFFERENTIAL GLOSS MEASURING SYSTEM

(75) Inventors: Martin E. Banton, Fairport, NY (US); Dale R. Mashtare, Bloomfield, NY (US); Paul A. Hosier, Rochester, NY (US)

(73) Assignee: Xerox Corporation, Norwalk, CT (US)

( * ) Notice: Subject to any disclaimer, the term of this patent is extended or adjusted under 35 U.S.C. 154(b) by 0 days.

(21) Appl. No.: 11/783,174

(22) Filed: Apr. 6, 2007

(65) Prior Publication Data

US 2008/0245979 A1 Oct. 9, 2008

(51) Int. Cl.
*G01N 21/86* (2006.01)

(52) U.S. Cl. .............................. 250/559.4; 250/559.16; 356/446

(58) Field of Classification Search .............. 250/559.4, 250/559.16; 356/446
See application file for complete search history.

(56) References Cited

U.S. PATENT DOCUMENTS

| | | | |
|---|---|---|---|
| 4,945,253 A | | 7/1990 | Frohardt |
| 5,101,285 A | * | 3/1992 | Kawai et al. ................ 358/471 |
| 5,162,874 A | | 11/1992 | Butler ........................ 356/446 |
| 5,204,538 A | | 4/1993 | Genovese ................... 250/571 |
| 5,555,084 A | * | 9/1996 | Vetromile et al. ............ 399/16 |
| 5,556,529 A | * | 9/1996 | Nemoto ...................... 204/612 |
| 5,654,799 A | | 8/1997 | Chase et al. |
| 5,748,221 A | | 5/1998 | Castelli et al. .............. 347/232 |
| 5,751,432 A | | 5/1998 | Gwaltney |
| 6,016,204 A | | 1/2000 | Budnik et al. |
| 6,240,205 B1 | | 5/2001 | Fan et al. |
| 6,242,145 B1 | | 6/2001 | Galloway et al. |

(Continued)

OTHER PUBLICATIONS

Anni Berger-Schunn, Practical Color Measurement: A Primer for the Beginner, a Reminder for the Expert, Wiley Series in Pure and Applied Optics, authorized translation of the German edition published by John Wiley & Sons, Inc., 1994.

(Continued)

*Primary Examiner*—Georgia Y Epps
*Assistant Examiner*—Kevin Wyatt
(74) *Attorney, Agent, or Firm*—Pillsbury Winthrop Shaw Pittman LLP

(57) ABSTRACT

A system is provided for measuring gloss and spatial dependence of gloss. In a first embodiment, the system comprises: a first illuminator configured to emit a first light beam at a point on a target, thereby producing a generally specular reflectance in a first direction; a second illuminator configured to emit a second light beam at the point on the target, thereby producing generally diffuse reflectance in the first direction; a linear array sensor configured to detect the generally specular reflectance and the generally diffuse reflectance in the first direction; and a processor configured to process the generally specular reflectance and the generally diffuse reflectance detected by the linear array sensor. In a second embodiment, the system comprises: an illuminator configured to emit a beam of light at a point on a target, thereby producing a generally specular reflectance in a first direction and generally diffuse reflectance in a second direction; a first linear array sensor configured to detect the generally specular reflectance in the first direction; a second linear array sensor configured to detect the generally diffuse reflectance in the second direction; and a processor configured to process the generally specular reflectance detected by the first linear array sensor and the generally diffuse reflectance detected by the second linear array sensor.

15 Claims, 3 Drawing Sheets

U.S. PATENT DOCUMENTS

| | | | |
|---|---|---|---|
| 6,294,327 B1 * | 9/2001 | Walton et al. | 435/6 |
| 6,347,153 B1 | 2/2002 | Triplett et al. | |
| 6,526,250 B1 | 2/2003 | Usui et al. | |
| 6,975,949 B2 | 12/2005 | Mestha et al. | 702/76 |
| 7,024,152 B2 | 4/2006 | Lofthus et al. | 399/391 |
| 7,136,616 B2 | 11/2006 | Mandel et al. | 399/388 |
| 7,324,241 B2 | 1/2008 | Eschbach et al. | |
| 2003/0127006 A1 * | 7/2003 | Majewicz et al. | 101/483 |
| 2003/0128362 A1 * | 7/2003 | Gudaitis et al. | 356/405 |
| 2004/0001233 A1 | 1/2004 | Wang et al. | |
| 2004/0141764 A1 * | 7/2004 | Runkowske et al. | 399/38 |
| 2005/0083530 A1 * | 4/2005 | Ogihara et al. | 356/446 |
| 2005/0092724 A1 * | 5/2005 | Warren et al. | 219/121.85 |
| 2005/0200866 A1 | 9/2005 | Hoshii et al. | |
| 2005/0201223 A1 | 9/2005 | Bolash et al. | |
| 2006/0023266 A1 * | 2/2006 | Ohara | 358/474 |
| 2006/0046180 A1 | 3/2006 | Sanders et al. | |
| 2006/0092412 A1 | 5/2006 | Doshoda et al. | |
| 2006/0110009 A1 | 5/2006 | Klassen et al. | |
| 2006/0222384 A1 | 10/2006 | Moore et al. | 399/38 |
| 2007/0003302 A1 | 1/2007 | Mizes | 399/49 |
| 2007/0140571 A1 | 6/2007 | Fan et al. | |
| 2008/0173799 A1 | 7/2008 | Herloski et al. | |
| 2008/0291507 A1 | 11/2008 | Rodrigues et al. | |

OTHER PUBLICATIONS

Edul N. Dalal et al., "The Effect of Gloss on Color," Color Research and Application, Wiley InterScience, vol. 24, No. 5, Oct. 1999, pp. 369-376.

John C. Briggs et al., "The Effect of Fusing on Gloss in Electrophotography," IS&T's NIP14 International Conference on Digital Printing Technologies, Oct. 18-23, 1998, Toronto, Ontario, Canada, 6 pages.

* cited by examiner

GLOSS AND DIFFERENTIAL GLOSS MEASURING SYSTEM

FIELD

This invention relates to systems for measuring a surface characteristic, in particular, gloss and differential gloss.

BACKGROUND

In a printing system where multiple marking engines are used to print a job, consistency in image quality produced by the individual marking engines that are used to produce a given document is a central issue. It is important that the level of gloss be essentially the same, even though the pages (often it will be multiple copies of the same page) are printed on different marking engines. And, in systems with only one marking engine, it is important that gloss be uniform over a page.

U.S. Pat. No. 5,748,221, herein incorporated by reference, discloses measuring in situ color, gloss and registration, but at low resolution and at only one place in the process direction.

The inventors have recognized that it would be desirable to provide an improved way to assess the current gloss capability of each of the color engines. The inventors also recognized that it would be desirable to provide an improved way to assess the current gloss capability of each of the monochrome engines.

SUMMARY

In a first embodiment, the system comprises: a first illuminator configured to emit a first light beam at a point on a target, thereby producing a generally specular reflectance in a first direction; a second illuminator configured to emit a second light beam at the point on the target, thereby producing generally diffuse reflectance in the first direction; a linear array sensor configured to detect the generally specular reflectance and the generally diffuse reflectance in the first direction; and a processor configured to process the generally specular reflectance and the generally diffuse reflectance detected by the linear array sensor.

In a second embodiment, the system comprises: an illuminator configured to emit a beam of light at a point on a target, thereby producing a generally specular reflectance in a first direction and generally diffuse reflectance in a second direction; a first linear array sensor configured to detect the generally specular reflectance in the first direction; a second linear array sensor configured to detect the generally diffuse reflectance in the second direction; and a processor configured to process the generally specular reflectance detected by the first linear array sensor and the generally diffuse reflectance detected by the second linear array sensor.

In the first embodiment, the sampling of the sensor may be configured to synchronize the first and second illuminators so that each scanline of the sensor is alternately a capture of 1) a combination of the generally specular and the generally diffuse reflectance; and 2) the generally diffuse reflectance. The first illuminator can be configured to be pulsed on and off and the second illuminator can be configured to remain on.

The linear array sensor(s) may be a full width array sensor, contact image sensor, or a CCD array sensor, while the illuminator(s) may be a linear LED array, a lamps, a lamp with a reflector, or a collimated light source.

The processor may be configured to take in account any angular dependence of the illuminator(s) and the sensor(s).

The system may further comprises a cylindrical lens, baffles, field stops, or a combination thereof, placed in the optical path of the beam emitted by the illuminator used to produce the generally specular reflectance. Also, a Selfoc® lens may be placed in the optical path of the generally specular reflectance; wherein the Selfoc® lens is capable of being operated out of focus.

Multiple illuminators, each configured to emit a light beam at the point on the target, thereby producing generally diffuse reflectance may be used also. The various illuminators used may emit different spectral content.

Also, the angular dependence of the illuminator(s) and sensor(s), may be selectively adjustable.

Other objects, features, and advantages of one or more embodiments of the present invention will seem apparent from the following detailed description, and accompanying drawings, and the appended claims.

BRIEF DESCRIPTION OF THE DRAWINGS

Embodiments of the present invention will now be disclosed, by way of example only, with reference to the accompanying schematic drawings in which corresponding reference symbols indicate corresponding parts, in which.

DETAILED DESCRIPTION

The law of reflection states that the direction of outgoing reflected light and the direction of incoming light make the same angle with respect to the surface normal. Specular reflection is the perfect, mirror-like reflection of light from a surface, in which light from a single incoming direction is reflected into a single outgoing direction. In contrast, diffuse reflection is reflection of light from a surface, in which light from a single incoming direction is reflected in many directions, due to surface irregularities that cause the rays of light to reflect in different outgoing directions. The type of reflection depends on the structure of the surface. For example, while both matte and glossy prints exhibit a combination of specular and diffuse reflection, matte prints have a higher proportion of diffuse reflection and glossy prints have a greater proportion of specular reflection.

Figure 2:
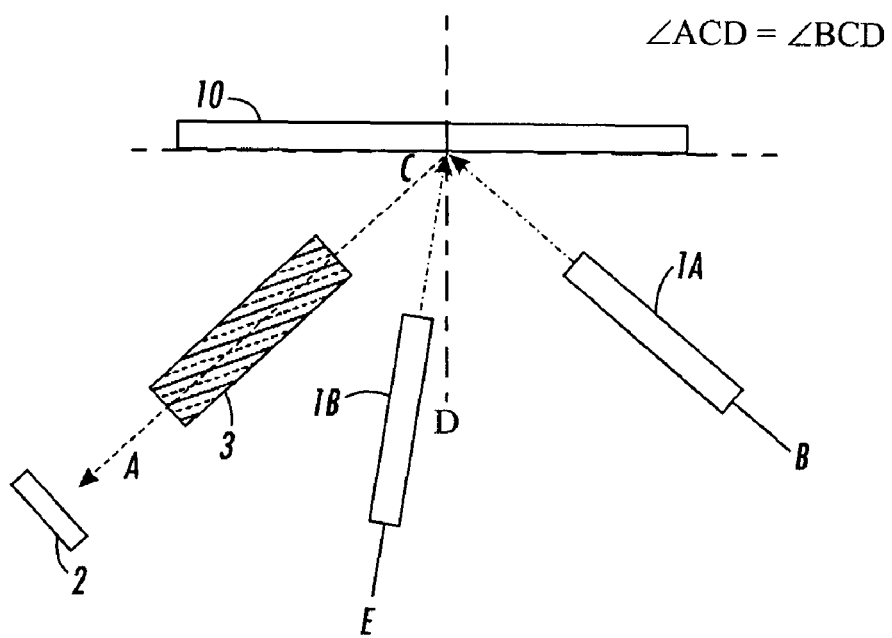
FIG. 2 shows an embodiment of the invention having two illuminators and one sensor, where the illuminators are arranged on the same side of the sensor, in accordance with the invention.
Figure 3:
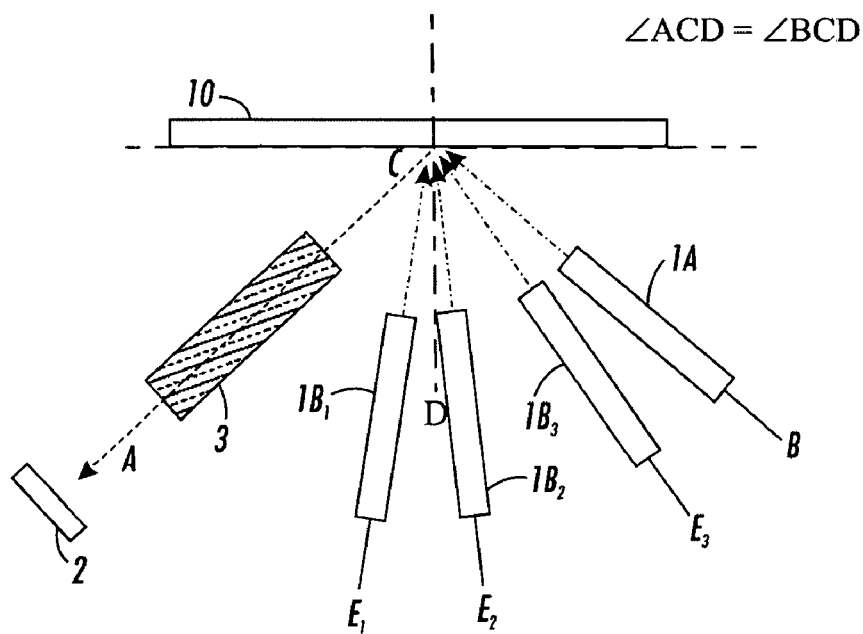
FIG. 3 shows an embodiment of the invention having at least three illuminators and one sensor, in accordance with the invention.

A system is provided for gloss sensing and for measuring the spatial dependence of gloss. Advantageously, the system is configured to capture high spatial resolution that is available in both the process and cross-process (or fast scan) directions. In a first embodiment, as shown in FIGS. 1-3, the system includes at least two separate illuminators 1A and 1B in conjunction with a sensor 2.

Preferably, the sensor 2 is a linear array sensor, for example, a full width array (FWA) sensor. A full width array sensor may include a plurality of sensors equally spaced at intervals (e.g., every 1/600th inch (600 spots per inch)) in the cross-process direction. See for example, U.S. Pat. No. 6,975,949, incorporated herein by reference. It is understood that other linear array sensors may also be used, such as contact image sensors or CCD array sensors.

Figure 6:
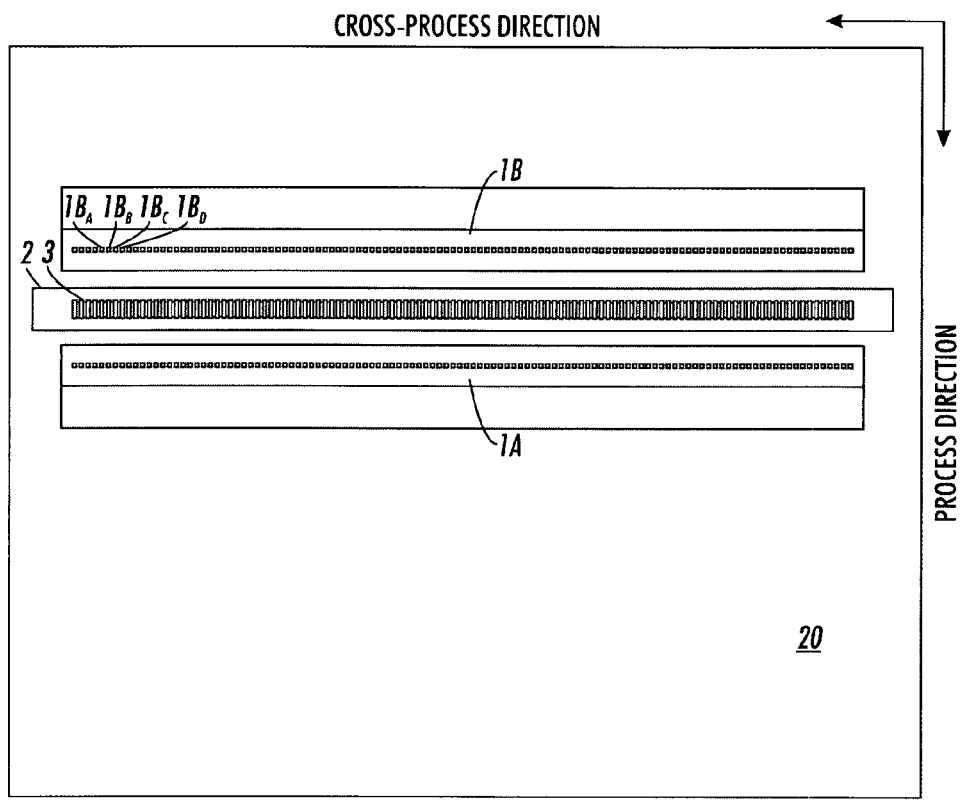
FIG. 6 shows an embodiment of the invention, configured to capture high spatial resolution in both the process and cross-process directions, in accordance with the invention.

The sensor 2 is configured to detect the reflectance of light from a generally smooth and flat surface of a target 10. The target may preferably be any printing or scanning surface. Line C-D represents a normal line to the surface at a point C of the target 10. Point C may actually be a line or region on the surface of the target (for example as shown in FIG. 6).

Figure 1:
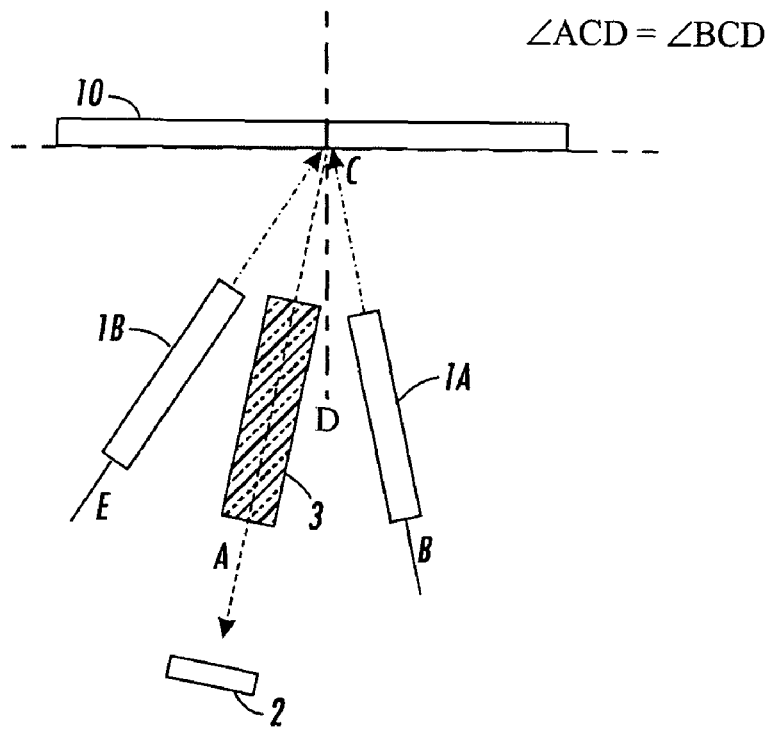
FIG. 1 shows an embodiment of the invention having two illuminators and one sensor, where the illuminators are arranged on opposite sides of the sensor, in accordance with the invention.

In FIG. 1, the first illuminator 1A is located on a line B-C, while the second illuminator 1B is located on a line E-C. The angle ($\angle ACD$) between lines A-C and D-C is set to be substantially equal to the angle ($\angle BCD$) between lines B-C and C-D, such that the first illuminator 1A is configured to emit a light beam onto the target 10 at point C, thereby producing a generally specular reflectance from the target in a first direction along line A-C.

The angle ($\angle ECD$) between lines E-C and D-C is set to be some angle other than the angle ($\angle ACD$) between lines A-C and D-C, such that the second illuminator 1B is configured to emit a light beam onto the target 10 at point C, thereby producing some generally diffuse reflectance in at least the first direction along line A-C.

The sensor 2 is located along a line A-C, such that it captures the generally specular reflectance from the first illuminator 1A, as well as, some of the diffuse reflectance from the second illuminator 1B, both reflected from point C of the target 10 in the first direction. Because the surface of the target 10 will never be a "perfect mirror," the specular reflectance from the beam of illuminator 1A along line A-C will also include some (albeit a small fraction of) diffuse reflectance from the beam of illuminator of 1A.

The illuminators 1A, 1B are implemented as light sources. Preferably, a linear LED array may be used in conjunction with the linear array sensor 2, as disclosed, for example, in U.S. Pat. No. 6,975,949, previously mentioned above. The linear LED array could also use just one row of LEDs. The combination of a linear array sensor and linear LED array allows for high spatial resolution (e.g., 600 spi) in both the process and cross-process directions. The LED arrays could be all one color, e.g., white or of multiple colors, as described in U.S. Pat. No. 6,975,949. Also, the illuminators may be lamps, or may consist of a lamp on side of the linear array sensor and a reflector on the other side. A collimated light beam may yield a greater of ratio of specular reflectance.

It may be possible to have the two illuminators 1A, 1B emit light with different spectral content, should that be desirable. If the illuminators 1A, 1B consist of red, green and blue LEDs, the spectral content could be tailored in the field to the application at hand.

The illuminators can be turned on and off in a time that is less than or equal to a line time for a predetermined spatial resolution in the process direction. It is likely that one of the illuminators, for example, the diffuse illuminator 1B may be left on and only the specular illuminator 1A is pulsed on and off. The types of illuminators may be different, for example, the illuminator used for the specular reflectance could be a lamp while the illuminator used for the diffuse reflectance could consist of a red, green, blue and other color LEDs.

Two embodiments relying of two illuminators 1A, 1B and one sensor 2 with a Selfoc® lens 3 are shown in FIGS. 1 and 2. The key difference between the embodiments shown in FIGS. 1 and 2 is in the placement of the two illuminators 1A, 1B relative to the sensor 2. In FIG. 1 the two illuminators 1A, 1B are on opposite sides of the sensor 2. In contrast, in FIG. 2 the illuminators 1A, 1B are both on the same side of the sensor 2.

A cylindrical lens arrangement (not shown) may also be placed in the optical path of the specular illuminator 1A to minimize diffuse illumination, further reduced with baffles and/or field stops, along the illumination width. Ideally, collimation of the specular illuminator 1A would help to insure more sharply defined specular image capture.

The sampling of the sensor 2 may be synchronized to the illuminators 1A, 1B so that each scanline is alternately a capture of: 1) diffuse reflectance; and 2) the combination of specular and diffuse relfectances. For example, the two illuminators 1A, 1B can be pulsed on and off sequentially so that scanline N will be a capture of diffusely reflected light and scanline N+1 will be a capture of the combination of specularly and diffusely reflected light, thereby producing two images. Given a system capable of 600 scans per inch (spi) sampling in the process direction, the output would be two 300 spi images, one the combination of specular and diffuse reflection and one the diffuse reflection. From these images that have half the normal 600 spi resolution, a full resolution image for each of the two cases could be generated. It is likely that in many, if not for most of the applications, the fact that the two images are interdigitated will not introduce complications that require attention. In fact, low resolution scanning may even be an advantage, if the primary application is for gloss measurement uniformity.

If the primary application is for gloss uniformity only, then the sensor 2 could likely work at a much lower resolution, e.g., 200 spi, 100 spi or even 50 spi. The specular and diffuse images can be compared to the content of the image that was printed on a given page. The comparison of the measured gloss pattern to the image content of the page enables identification of whether or not the gloss is as uniform as it should be. Given knowledge of diffuse and specular components, one can determine the true specular reflection in situations where that is desirable.

Since, there are two signals, one a measure of the diffusely reflected light and the other a measure of the specularly and diffusely reflected light, it is possible to extract the pure specular component when separate knowledge of the specular component is required. Knowing the angles of operation of the two illuminator-sensor combinations enables any angular dependence to be taken into account. For example, test patterns can be generated to test the gloss performance of a fuser by matching the amount of specularly reflected light from a fused print. Knowledge of the test pattern combined with the specular reflection measurement would show how the fuser is performing across and along the process for selected colors. It is also possible to measure the gloss level of customer images knowing the amounts of toner that have been laid down to print the image and to ensure uniformity.

Another control parameter in the system is how well the Selfoc® lens 3 is focused. It may be advantageous to operate the Selfoc® lens 3 out of focus, which can be easily implemented in providing a mechanism (not shown) for controlling the amount the Selfoc® lens is of out-of-focus. Thus, the focus can be changed and/or controlled in the printing system.

FIG. 3 shows an embodiment which uses at least three diffuse illuminators $1B_1$, $1B_2$, $1B_3$ located along respective axes $E_1$-C, $E_2$-C, $E_3$-C. The angles ($\angle E_1CD$, $\angle E_2CD$, ∠E₃CD) between lines E₁-C, E₂-C, E₃-C and normal line D-C are set to be some angles other than the angle (∠ACD) between lines A-C and normal line D-C, such that the multiple diffuse illuminators 1B₁, 1B₂, 1B₃ are each configured to emit a light beam onto the target 10 at point C, thereby producing some generally diffuse reflectance at least in a direction along line A-C.

Another embodiment (not shown), may be to have the angle for specular reflectance be variable by selecting one of a plurality of illuminators (for example as shown in FIG. 3), and changing the angle between the axis of the sensor and normal line to the surface of the target to match the angle between the axis of the selected illuminator and the normal line to the surface of the target. Further, the angle for diffuse reflectance could be variable also. The various angular relationships can be selectively adjusted by changing the angles of the sensor(s) and/or illuminator(s) with respect to the normal line, in order to change the angular dependence with respect to the specular and/or diffuse reflectances, should this be desirable.

In a further embodiment, it is also possible that the system may be used to read glossmarks. Optimization for the various applications can be done. For example, for measuring gloss marks the optimal angle between the detector and the illuminator could well be different from that required for other applications. Also, the type of calibrations that would be required can be determined by experimentation. For example, it may be advantageous to have two calibration strips, one with a matte finish and one with a glossy finish.

Figure 4:
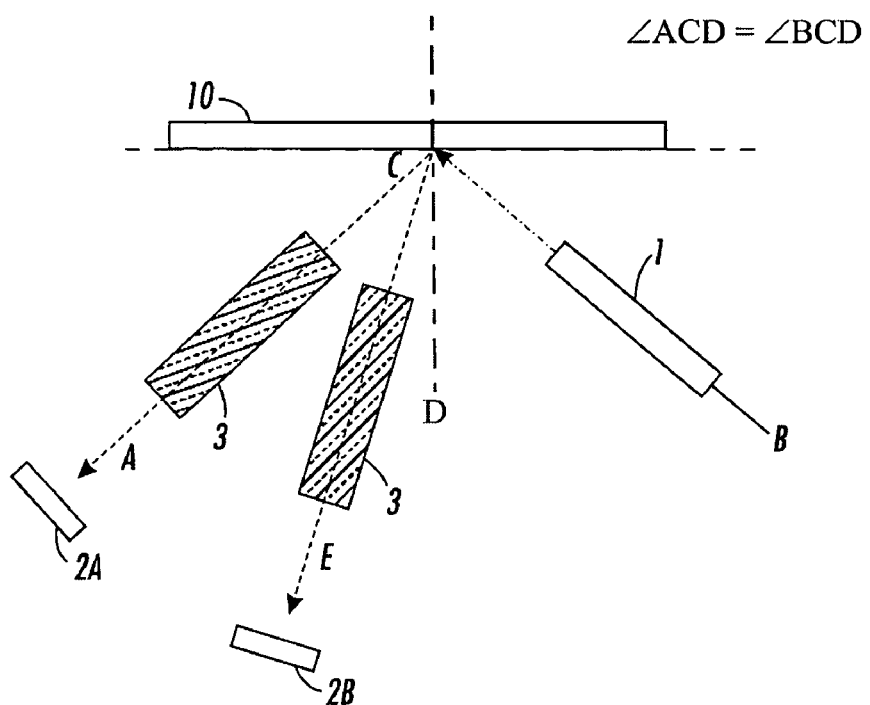
FIG. 4 shows an embodiment of the invention, having one illuminator and two sensors, in accordance with the invention.

While it is most likely that one would use multiple illuminators 1A, 1B as shown in FIGS. 1-3, it may be also possible to configure a system with a single illuminator 1 and two sensors 2A, 2B, as shown in FIG. 4.

A single illuminator 1 is located on a line B-C and configured to emit a light beam onto the target 10 at point C, which is reflected, thereby producing generally specular reflectance in a first direction along line A-C, and some generally diffuse reflectance at least in a second direction, e.g., along line E-C. The angle (∠ACD) between line A-C and normal line D-C is substantially equal to the angle (∠BCD) between line B-C and normal line D-C. In contrast, the angle (∠ECD) between line E-C and normal line D-C is some angle other than the angle (∠ACD) between line A-C and normal line D-C.

A first sensor 2A is located along line A-C, such that it captures the generally specular reflectance in the first direction reflected from the target 10 at point C. A second sensor 2B is located along line E-C, such that it captures the diffuse reflectance in the second direction reflected from the target 10 at point C. This embodiment provides full resolution images for both types of reflected light. A calibration procedure could be determined so that the signals from the two separate sensors 2A, 2B can be used to work out the true specular reflectance and the difference between the specular and diffuse reflectances of the image being measured.

Figure 5:
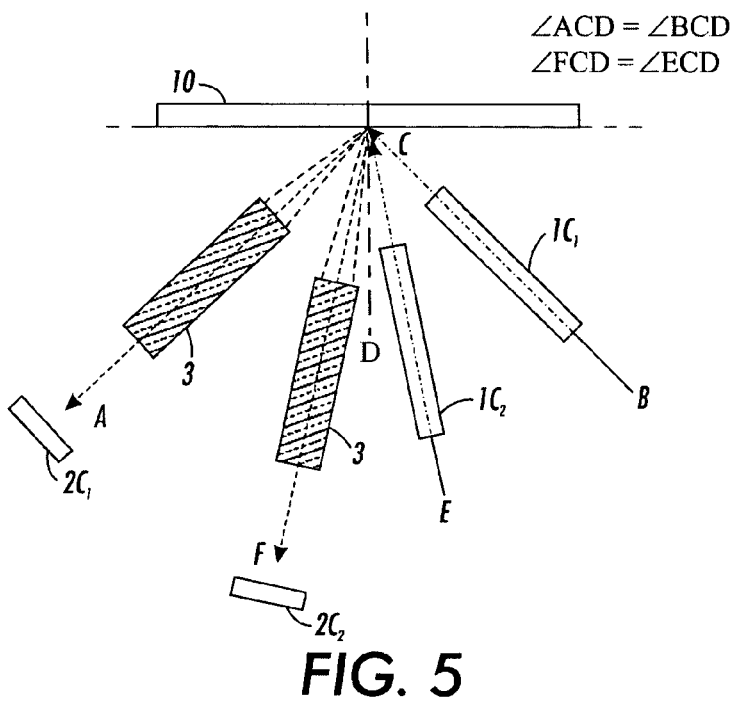
FIG. 5 shows an embodiment of the invention, having two illuminators and two sensors, in accordance with the invention.

This concept could be extended further, as shown in FIG. 5, to have two sensors 2C₁, 2C₂ located on lines A-C and F-C, respectively, and to have two illuminators 1C₁, 1C₂ located on lines B-C and E-C, respectively. The angle (∠ACD) between lines A-C and D-C is set substantially equal to the angle (∠BCD) between lines B-C and C-D; and the angle (∠ECD) between lines E-C and D-C is set substantially equal to the angle (∠FCD) between lines F-C and D-C. Angles (∠BCD) and (∠ACD) are not equal to angles (∠ECD) and (∠FCD). As such, the first sensor 2C₁ is in a position to capture the generally specular reflectance produced by the first illuminator 1C₁ and some generally diffuse reflectance produced by the second illuminator 1C₂. Similarly, the second sensor 2C₂ is in a position to capture the generally specular reflectance produced by the first illuminator 1C₂ and the some generally diffuse reflectance produced by the second illuminator 1C₁. This embodiment enables interdigitated capture of the generally specular and the generally diffuse reflectances produced by the two illuminators. Preferably, each illuminator produces different wavelengths, e.g., visible and infrared.

FIG. 6 shows an advantageous configuration for capturing high spatial resolution in both the process and cross-process (or fast scan) directions. The illuminators 1A, 1B may comprise two linear LED arrays, one configured to provided the generally specular illumination and the other to provide the generally diffuse illumination to the full width array sensor 2. (Note: FIG. 6 uses the embodiment of FIG. 1, however, it is understood that any of the embodiments disclosed herein may be used). The individual LEDs 1B_A, 1B_B, 1B_C, 1B_D, etc. of the LED arrays could be all of the same kind, or could be individually configured to produce different wavelengths or spectra, if this is desirable. By orienting the linear array sensor 2 in the cross-process direction, a high resolution measurement can be made over the entire width of target surface, e.g., a sheet of paper 20.

The system may be used in conjunction with a tightly integrated parallel printing (TIPP) system, where multiple printing machines are controlled to output a single print job, as disclosed in U.S. Pat. Nos. 7,136,616 and 7,024,152, herein incorporated by reference. The system may be configured to advantageously monitor fuser performance and match the performance of each of the multiple fusers in a TIPP system. Also, it can be used in overprinting in a TIPP system, for example as disclosed in U.S. Patent Application Publication No. 2006/0222384, herein incorporate by reference.

Tacking of the toned image can be accomplished by imparting only minimally incremental gloss to the toned regions as toner flows to promote tacking to the substrate. Having the ability to maintain the operation of the "tack" fusing is essential to control uniformity when marking on a page with more than one marking engine. In some of the TIPP systems a second fuser or FAP (Final Appearance and Permanence) station is used. The system may also be used to determine if each marking engine is operating in an optimal manner. If the fusing done in each of the marking engines or in some of the marking engines is delivering output at some specified gloss level, it may be desirable not to use the FAP on those pages.

In another embodiment, the system may also be used for scanning or reading (e.g., OCR) documents. This is especially true for the configuration shown in FIG. 1. In that case, the presence of the two illuminators 1A, 1B would help to minimize any shadowing at the edge of pages or paste-ups just like the use of an opposed reflector in copying applications where a sensor is used.

It is also possible to remove the diffuse reflectance from the combination of the specular and diffuse reflectance that is captured. This allows for a more accurate measurement of the specular reflectance, exclusive of other factors (e.g., the opacity of the target surface, or stray light, etc.), which will be removed with the diffuse reflectance. Since considerable filtering is already used to lower resolution of the system to 300 spi versus the normal 600 spi, this should not introduce artifacts.

A processor (not shown) is provided to both calibrate the sensor(s) and to process the reflectance data detected by the sensor(s). It could be dedicated hardware like ASICs or FPGAs, software, or a combination of dedicated hardware and software. For the different applications the basic algorithm for extracting the specular and diffuse components would be the same but the analysis for the particular applications would vary.

It is possible that some of the applications above could be performed with specular only, but the measurement would be more accurate and the algorithms used to extract the measures desired would be easier and less likely to introduce errors with both specular and diffuse reflectance information available.

While the specific embodiments of the present invention have been described above, it will be appreciated that the invention may be practiced otherwise than described. The description is not intended to limit the invention.

What we claim is:

1. In a printing device, a system for detecting a surface characteristic of a printable surface, comprising:
   a first illuminator configured to emit a first light beam at a point on a printable surface, thereby producing a generally specular reflectance in a first direction;
   a second illuminator configured to emit a second light beam at the point on the printable surface, thereby producing generally diffuse reflectance in the first direction;
   a linear array sensor configured to detect the generally specular reflectance and the generally diffuse reflectance in the first direction, wherein the linear array sensor is positioned substantially along a cross-process direction of the printing device; and
   a processor configured to process the generally specular reflectance and the generally diffuse reflectance detected by the linear array sensor and to determine a gloss characteristic of the printable surface,
   wherein sampling of the sensor is configured to synchronize the first and second illuminators so that each scanline of the linear array sensor is alternately a capture of 1) a combination of the generally specular and the generally diffuse reflectance; and 2) the generally diffuse reflectance.

2. The system of claim 1, wherein the linear array sensor is a full width array sensor, contact image sensor, or a CCD array sensor.

3. The system of claim 1, wherein the first illuminator, the second illuminator, or both, comprises at least one of the group consisting of: a linear LED array, a lamp, a lamp with a reflector, and a collimated light source.

4. The system of claim 1, wherein the generally specular reflectance in the first direction comprises some diffuse reflectance.

5. The system of claim 1, wherein the first illuminator is configured to be pulsed on and off and the second illuminator is configured to remain on.

6. The system of claim 1, wherein the processor is configured to take in account an angular dependence of the first illuminator, the second illuminator, the linear array sensor, or a combination thereof.

7. The system of claim 1, further comprising a cylindrical lens, baffle, field stop, or a combination thereof, placed in the optical path of the beam emitted from the first illuminator.

8. The system of claim 1, further comprising a Selfoc® lens placed in the optical path of the generally specular reflectance in the first direction.

9. The system of claim 8, wherein the Selfoc® lens is capable of operating out of focus.

10. The system of claim 1, wherein the second illuminator comprises a plurality of illuminators, each configured to emit a light beam at the point on the printable surface, thereby producing generally diffuse reflectance in the first direction.

11. The system of claim 1, wherein the first and second illuminators emit the same or different spectral content.

12. The system of claim 1, wherein at least one of the following is selectively adjustable:
   (i) the angle of the generally specular and diffuse reflectances in the first direction with respect to the line normal to the surface of the printable surface;
   (ii) the angle of the beam emitted from the first illuminator with respect to the line normal to the surface of the printable surface; and
   (iii) the angle of the beam emitted from the second illuminator with respect to the line normal to the surface of the printable surface.

13. The system of claim 12, wherein said angle is selectively adjustable by changing the angular dependence of at least one of the following:
   (i) the first illuminator;
   (ii) the second illuminator; and
   (iii) the linear array sensor.

14. The system of claim 1, further comprising a printing or marking device.

15. The system of claim 1, wherein the linear array sensor has a resolution of about 600 spots per inch in the cross-process direction.

* * * * *